United States Patent [19]

Bogen et al.

[11] 4,074,243
[45] Feb. 14, 1978

[54] ANTICIPATORY FLAMMABLE GAS DETECTION SYSTEM

[75] Inventors: John S. Bogen, Chicago; Gary I. Robin, Niles, both of Ill.

[73] Assignee: Erdco Engineering Corporation, Addison, Ill.

[21] Appl. No.: 697,452

[22] Filed: June 18, 1976

[51] Int. Cl.² ............................................. G08B 17/10
[52] U.S. Cl. ............................ 340/237 R; 340/248 A
[58] Field of Search ........... 340/237 R, 239 R, 248 A, 340/233; 23/232 E, 254 E, 255 E; 328/148

[56] References Cited

U.S. PATENT DOCUMENTS

| | | | |
|---|---|---|---|
| 2,827,624 | 3/1958 | Klein | 340/233 |
| 2,871,466 | 1/1959 | Vassil et al. | 340/233 |
| 2,901,740 | 8/1959 | Cutsogeorge | 340/233 |
| 3,038,106 | 6/1962 | Cutsogeorge et al. | 340/233 X |
| 3,594,557 | 7/1971 | Anderson | 340/237 R X |
| 3,748,656 | 7/1973 | Gray et al. | 340/248 A X |
| 3,978,462 | 8/1976 | Goodman | 340/239 R X |

Primary Examiner—John W. Caldwell, Sr.
Assistant Examiner—Daniel Myer
Attorney, Agent, or Firm—Darbo & Vandenburgh

[57] ABSTRACT

An anticipatory flammable gas detection system is provided for quickly determining whether the rise rate of gas concentration will approach a potentially hazardous level. The system includes a detector for determining the rise rate of the gas concentration and a comparator for determining whether the rise rate exceeds a potentially hazardous level. An integrator or multivibrator is provided for determining how long the rise rate exceeds a predetermined value. If the rise rate exceeds the predetermined hazardous rate of rise for more than a predetermined period of time, an alarm signal is generated. Prevention of false alarms is accomplished by providing another comparator which determines whether the magnitude of gas concentration exceeds a preselected percentage of the lower flammable limit. Should the magnitude be less than the preselected percentage, the alarm signal will not be generated.

9 Claims, 4 Drawing Figures

ANTICIPATORY FLAMMABLE GAS DETECTION SYSTEM

BACKGROUND AND SUMMARY OF THE INVENTION

This invention relates to detection apparatus, and more particularly, to a flammable gas detection system.

There are many gas detection systems and related equipment therefor such as found in U.S. Pat. Nos. 3,239,828; 3,522,010 and 3,665,240. Such prior art gas detection systems are useful in detecting the gas concentration level of a particular gas. In potentially hazardous areas, however, such as, for example, offshore platforms and chemical plants, it is highly desirable to have a detection system which not only indicates the concentration level of the gas, but also monitors the rate at which the gas concentration level is increasing in order to predict a hazardous condition before it occurs.

In some prior art gas detectors, it may take as much as 3½ to 6 seconds or more to determine the existence of a hazardous concentration level in a high velocity air stream. It may take as much as 30 seconds to determine a hazardous concentration level in a static air stream. By the time such gas detectors determine that the level of gas concentration exceeds the LFL level or is dangerously high, the condition is already hazardous. It is therefore very desirable to have a rapid response detection system, which can be used in locations where rapid concentration build-ups can occur, such as an offshore platform or a chemical plant where a rupture could cause large volumes of flammable gases or vapors to reach the inlet of a pressurized heating and air conditioning system servicing a nonhazardous area, so that the condition can be remedied before it reaches a hazardous level.

As used in this application, the terms "hazardous rise rate", "hazardous rate of rise" and "hazardous rate of change" refer to a changing gas concentration level which would become hazardous if allowed to continue unchecked.

One object of this invention is to improve the safety of potentially hazardous areas.

Another object of this invention is to provide a detection system and method for predicting whether the gas concentration will approach a hazardous level.

A further object of this invention is to provide an alarm signal responsive to an increasing gas concentration level which would become hazardous if allowed to continue unchecked.

Another object of this invention is to provide improved circuitry for preventing false alarms, so as to avoid expensive and inconvenient shut downs.

It is still another object of this invention to provide an improved detection system of relatively simple design and construction, which is easy to use and install and results in considerable economic saving.

In accordance with the present invention, a detection apparatus is provided for use in monitoring a quantity whose rise rate or growth is an exponential, hyperbolic or linear function. The detection apparatus includes detection means for detecting the rate of the change of the quantity and comparator means for comparing that rate of change with a preselected reference rate of change. Control means operatively responsive to the comparing means are provided for effecting a signal indicating that the rate of change of the quantity has exceeded the preselected reference rise rate.

The detection apparatus may include sensing means for determining the absolute magnitude of the quantity, and second comparator means for comparing the absolute magnitude of the quantity with a preselected reference magnitude. The control means may further include limiting means operatively connected to the second comparator means for effecting generation of a signal only when the absolute magnitude of the quantity exceeds the preselected reference magnitude.

The detection apparatus can be constructed and arranged to include integrating means for effecting a signal dependent upon the period of time in which the rate of change of the quantity exceeds a preselected reference rate of change. Third comparative means are provided for determining whether the period of time is greater than the preselected period of time. The control means may further include second limiting means for effecting generation of the signal only when the period of time of rate of change of the quantity surpasses the predetermined period of time.

Furthermore, the detection apparatus may include selection means for determining the reference rate of change in response to preselected threshold and asymptotic values.

In the illustrated embodiment, a flammable gas detection system is provided with sensing means for determining the concentration level of a flammable gas. The sensing means includes a transducer for effecting an indicating signal proportional to the concentration of the gas. A differentiator is provided for generating a rate of change signal proportional to a preselected reference rate of change. Comparator means are provided for comparing the rate of change signal with the reference signal. Control means, operatively responsive to the comparing means, energizes an alarm signal, when the rate of change of the sensed gas concentration exceeds the reference rise rate.

In another embodiment, the flammable gas detection system includes means for effecting a reference signal porportional to a hazardous rate of change of the gas concentration level, including a threshold signal proportional to a preselected threshold value and an asymptotic signal proportional to a preselected asymptotic value. Comparator means are provided for comparing the gas concentration signal with the reference signal to determine if the rate of change of concentration of the sensed gas exceeds the hazardous rate of change.

The present invention also contemplates a method for monitoring a quantity, such as a flammable gas concentration, whose rise rate or growth is an exponential, hyperbolic or linear function. The method includes the steps of detecting the rise of the quantity, comparing the rate of change of the quantity with a reference rate of change effecting a signal when the rate of change of the quantity exceeds the reference rate of change.

A more detailed explanation of the invention is provided in the following description and claims and illustrated in the accompanying drawings.

DESCRIPTION OF SPECIFIC EMBODIMENT

Figure 2:
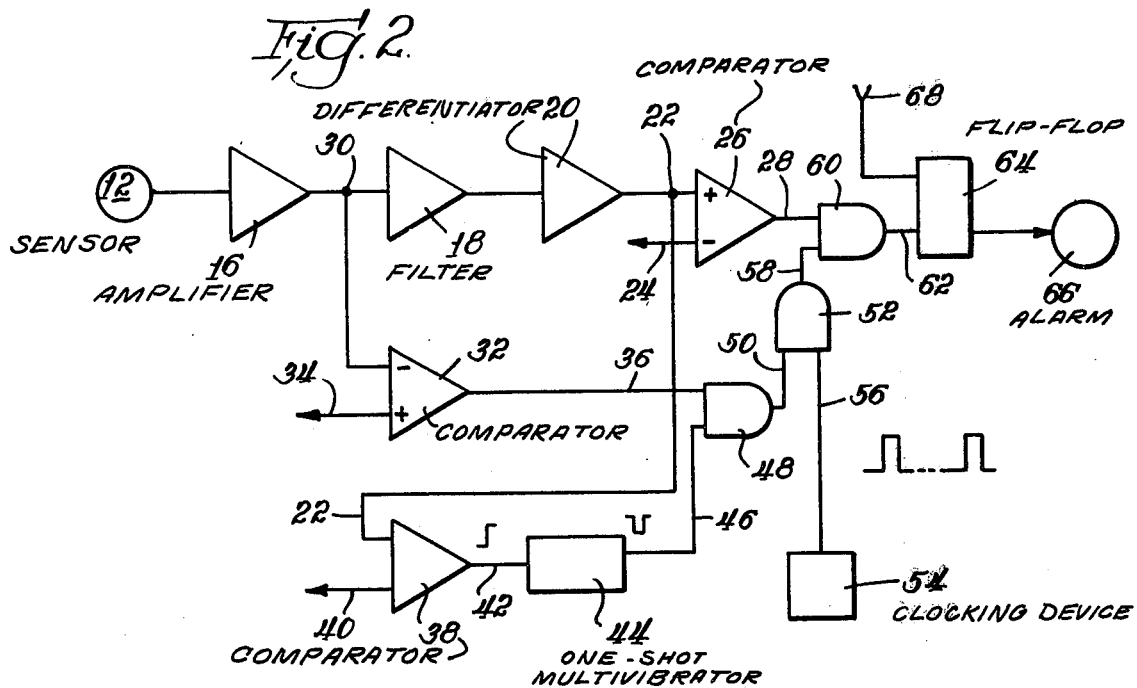
FIG. 2 is a functional diagram of an anticipating flammable gas detection system in accordance with principles of the present invention.

Referring to the drawings, an anticipating flammable gas detection system, as best shown in FIG. 2, includes a sensor or transducer 12 for sensing the concentration of a gas, such as methane, and for producing a signal proportional to the concentration of the gas. For methane, 170 millivolts may represent approximately 100% of the lower flammable limit (LFL) of methane. At atmospheric pressure and other normal ambient conditions, the lower flammable limit for methane is 5% by volume with air.

A linear amplifier 16 is connected to the transducer 12. The amplified signal from the linear amplifier is fed through a filter 18 to a differentiator 20. The differentiator produces a signal proportional to the rate of increase of the gas concentration. The output level 22 of the differentiator is thus proportional to the rise rate of the sensed gas concentration.

A selectable reference voltage 24 is proportionally related to be representative of a predetermined percentage of the rise rate of gas concentration. The reference voltage 24 is fed to a comparator 26 which compares the representative voltage at input 22 to the representative voltage at input 24. The output 28 of the comparator indicates whether the rise rate of sensed gas is greater or less than the reference rise rate.

A signal 30 proportionately related to the gas concentration level is fed to a comparator 32. Also fed to comparator 32 is a selectable reference voltage 34 corresponding to a percentage of the lower flammable limit. The voltage 34 is proportional to a preselected hazardous threshold level of the gas, which may be selected, for example as 15% LFL for methane. The output of the comparator 32 indicates whether the gas concentration level is greater than or less than the reference LFL level.

The DC output 22 of differentiator 20 is also fed to a comparator 38 which also receives a selectable reference voltage 40 proportional to another preselected reference rise rate. Output 42 of comparator 38 indicates whether the rise rate of gas concentration is greater or less than the reference rise rate 40 and is fed to a one-shot multivibrator 44. If the rise rate of gas concentration exceeds the reference rise rate, then the one-shot multivibrator will generate an output signal 46 which indicates that the rate of rise has occurred for the entire preselected period of time.

An AND gate 48 receives signals 36 and 46 and will produce an output signal 50 to AND gate 52 when (1) the gas concentration level indicated by signal 36 is greater than the reference LFL level indicated by signal 34, and (2) the rise rate of the sensed gas has occurred for the entire predetermined period of time.

A clocking device 54 sends a clocking impulse or voltage signal 56 to AND gate 52. A high level logic output signal 58 from AND gate 52 is produced when input signals 50 and 56 are present at the AND gate 52. The output voltage signal 58 and the output signal 28 of comparator 26 are fed to an AND gate 60 which produces an output signal 62 to trigger flip flop 64 when:

(1) the rise rate of the sensed gas exceeds the preselected rise rate, (2) the gas concentration rate exceeds the reference LFL level, and (3) the rise rate of the sensed gas occurs for a preselected period of time. When the flip flop is set, an alarm relay coil 66 is energized. The alarm relay provides an alarm signal which may be reset by reset button 68.

Figure 1:
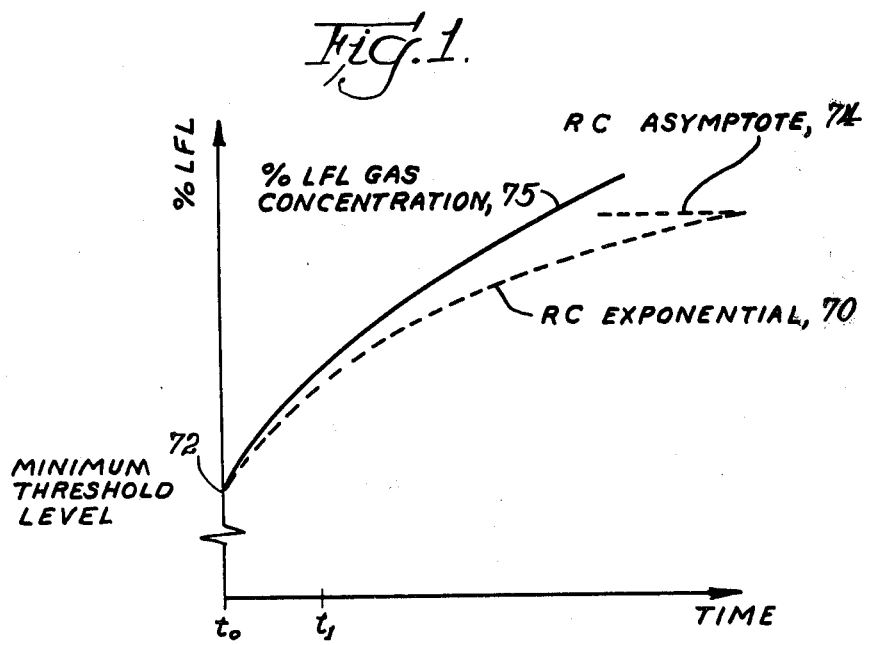
FIG. 1 is a chart illustrating in solid line the gas concentration level as a function of time and illutrating in broken line or phantom an RC exponential function simulating a rate of rise of the gas.

A typical RC exponential graph 70 as shown in FIG. 1 simulates a hazardous rise rate of gas concentration and generally indicates the percentage LFL versus time. The potentially hazardous rise rate begins at a minimum threshold level 72 and reaches an RC asymptote 74 as the curve approaches infinite time. An example of a flammable gas being sensed is shown by the gas concentration curve 75, which in the example shown in FIG. 1, exceeds the preselected hazardous rise rate. When desired, graph 70 may be linear.

Figure 3:
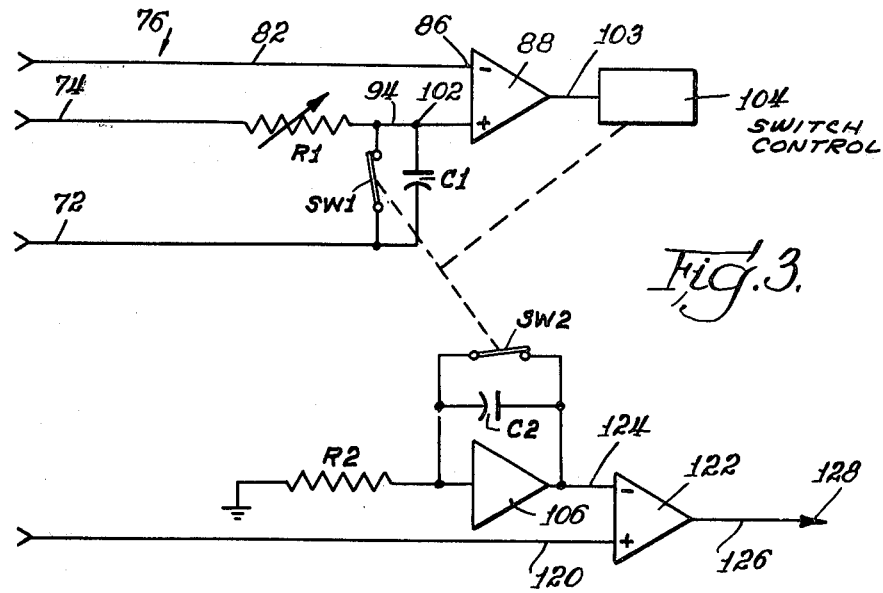
FIG. 3 is a functional diagram of a modified embodiment of an anticipating flammable gas detection system in accordance with principles of the present invention.
Figure 4:
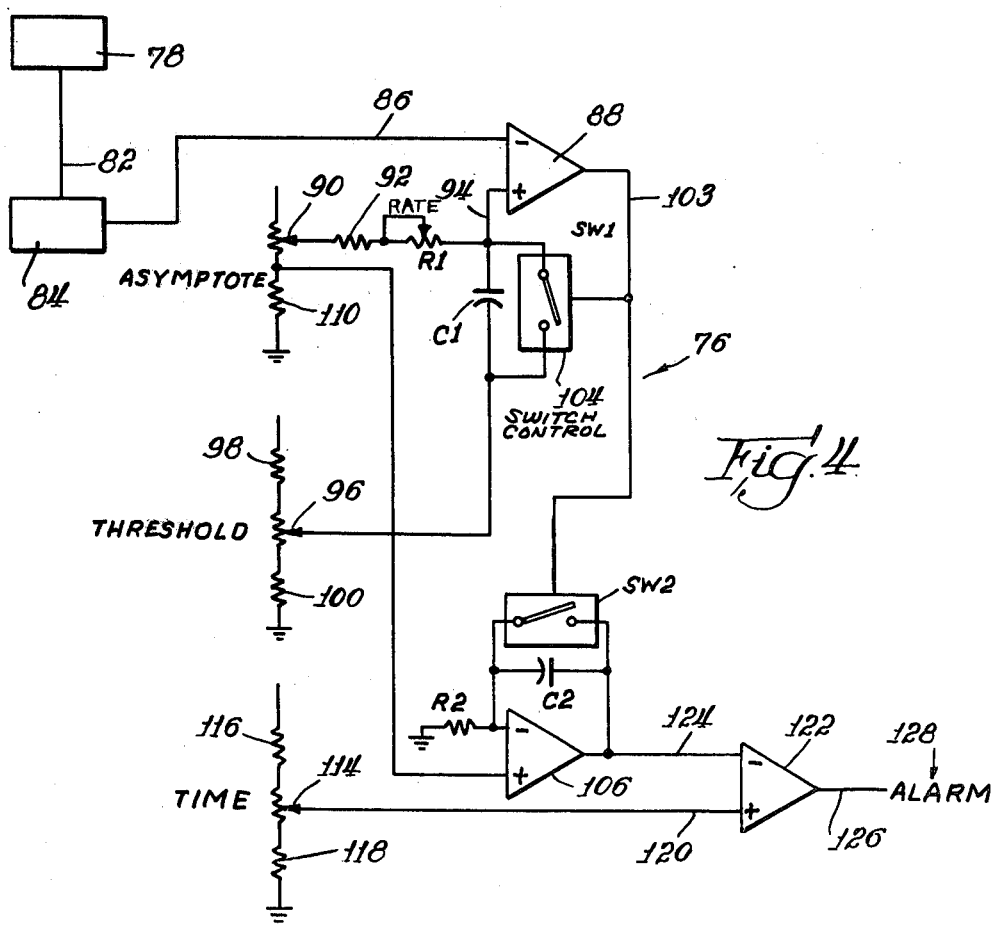
FIG. 4 is a schematic diagram of the modified embodiment of the anticipating flammable gas detection system.

Referring to FIGS. 3 and 4, a modified embodiment of an anticipating flammable gas detection system 76 includes a sensor or transducer 78 for sensing the concentration level of a gas such as methane and which produces an output voltage 82 proportional to the gas concentration level. A signal conditioner 84 is used to interface the sensor with the rest of the system. The output 86 of the signal conditioner is fed to a comparator 88.

The combination of a potentiometer 90 with resistor 110 proportions the voltage leading to comparator input 94 to the asymptotic value 74 of the hazardous rise rate concentration curve 70 as shown in FIG. 1. The combination of a variable resistor R1 and resistor 92 determines the rate at which the capacitor C1 will charge to the asymptotic value (74 in FIG. 1).

A potentiometer or voltage divider 96 in combination with resistors 98 and 100 is connected to capacitor C1 for producing an output signal 102 which is proportional to the minimum threshold value 72 of the hazardous rise rate curve 70 of FIG. 1. The output signal 102 is also fed to comparator 88. The values of R1 and capacitor C1 are selected to produce the desired exponential growth curve 70 which is proportional to the minimum hazardous rate of rise.

The output 103 of comparator 88 is connected to a switch control 104, which includes a normally closed switch SW1 connected in parallel with capacitor C1, and another normally closed switch SW2 connected in parallel with capacitor C2 and amplifier 106. Switch SW1 will remain closed if the output signal 103 of comparator 88 indicates that the gas concentration level, signal 86, is less than the threshold level. When the gas concentration level exceeds the threshold level, the output signal 103 will cause switch control 104 to open switch SW1. Once switch SW1 is open, comparator 88 compares the increasing rate of gas concentration signal 86 with the hazardous rise rate, signal 94, approaching asymptote 74 of FIG. 1. If at any time the gas concentration level of the sensed gas falls below the threshold value 72, as shown in FIG. 1, or the rise rate of the sensed gas falls below the hazardous rise rate, switch SW1 will close, discharging capacitor C1 instantaneously, so that the input signal into comparator 88 will once again be proportional to the minimum threshold voltage. Thus, switch SW1 remains open as long as the gas concentration exceeds threshold level and the rise rate of the sensed gas exceeds the hazardous rise rate.

The integrator, defined by the combination of resistor R2, amplifier 106, capacitor C2 and switch SW2, produces a linear voltage ramp at input 124 for the time interval during which switch SW2 is open.

A potentiometer 114 in series with resistors 116 and 118, proportions a voltage at input 120 corresponding to a selected time interval. This proportioned voltage is fed to comparator 122 as is the voltage ramp at input 124. The comparator 122 produces a first voltage output when the time in which the rise rate of the sensed gas exceeds the hazardous rise rate is greater than the preselected time interval, and produces a second voltage output when the time in which the rise rate of sensed gas exceeds the hazardous rise rate is less than the preselected time interval. When the output 126 of comparator 122 indicates that the time of rise rate is greater than the preselected time interval, alarm 128 will be activated. If the time during which the rise rate occurs is less than the predetermined time interval, SW2 and SW1 close, instantaneously discharging capacitors C1 and C2.

The alarm signal operates as a control which can be used for switching off machinery including a generator, or activating a blower or other devices such as audible and visual alarms.

By way of example, with no limitations indicated thereby, the parameters of the threshold may range from 1 to 10 percent LFL; the asumptote can range 50 to 150% LFL; the exponential growth rate can be generally selected from about 0.1 to about 3 seconds; and the predetermined time interval may be generally selected from about 0.1 second.

The flammable gas detection system is particularly useful in conjunction with an offshore platform, where a sensor or sensing head can be installed in the fresh air duct used to pressurize the control room. By coupling the flammable detection system with standard bridge circuitry, the flammable gas detection system can successfully monitor the fresh air duct, so that the control room of the offshore platform remains a non-hazardous area not requiring explosion-proof instruments and equipment. This system and arrangement makes it possible to achieve an alarm at a relatively low gas concentration level, if the gas concentration rate of rise exceeds the predetermined hazardous rise rate.

Among the many advantages of the anticipating flammable gas detection system is the ability to increase the safety of a potentially hazardous environment, such as an offshore drilling platform or a chemical plant. It has been found that when the flammable gas detection system monitors methane, the system requires only about one-half second to trigger an alarm. The combination of comparing the curve and the time of the fast rise rates prevents false alarms due to intermittent non-hazardous gas surges or "puffs" or from extraneous signals.

While the rate detector is particularly useful in detecting the rate of rise of flammable gas concentration, it can also be used to measure any quantity whose characteristic is a time related function, such as, but not limited to, acceleration, fluid flow rate, changes in temperature, run-away conditions at nuclear reactor plants, and pressure changes. Furthermore, while various voltage signals have been used in the flammable gas detection system, it may be desirable under some circumstances to use other proportional parameters such as current, pulse repetition rate, pulse width, pulse amplitude or pulse slope.

Although embodiments of the invention have been shown in the described, it is to be understood that various modifications and substitutions may be made by those skilled in the art without departing from the novel spirit and scope of the invention.

We claim:

1. A flammable gas detection system, comprising, in combination:
    flammable gas sensing means for sensing the flammable gas concentration level of a mixture of flammable and non-flammable gas, said flammable gas sensing means including a transducer for effecting an indicating signal proportional to said flammable gas concentration level;
    a differentiator for generating a rate of change signal in response to the rate of change of said flammable gas concentration level;
    reference signal means for effecting a continually changing reference signal which varies as a function of time, said continually changing reference signal being proportional to a non-constant preselected reference rate of change of flammable gas concentration level which varies as a function of time;
    comparator means for comparing the rate of change signal with the continually changing reference signal; and
    control means operatively responsive to the comparing means for energizing an alarm signal when the rate of change of the flammable gas concentration level exceeds the non-constant preselected reference rate of change of said flammable gas concentration level.

2. A flammable gas detection system as in claim 1 further including second reference signal means for effecting a second reference signal proportional to a preselected flammable gas concentration level, second comparator means for comparing the indicator signal with the second reference signal, and said control means further including first limiting means responsive to the second comparator means for effecting the alarm signal only when the magnitude of the flammable gas concentration level exceeds the preselected flammable gas concentration level.

3. A flammable gas detection system as in claim 2 further including means for determining whether the rate of change of flammable gas concentration level occurs for a preselected period of time, and said control means further includes second limiting means responsive to said means for effecting the alarm signal only when the rate of change of flammable concentration level occurs for the predetermined period of time.

4. A flammable gas detection system, comprising, in combination:
    flammable gas sensing means for sensing the flammable gas concentration level of a mixture of flammable and non-flammable gas, said flammable gas sensing means including a transducer for effecting a gas concentration signal proportional to said flammable gas concentration level;
    hyperbolic reference signal means for effecting a hyperbolic reference signal as a function of time, said hyperbolic reference signal being proportional to preselected hyperbolic hazardous rate of change of flammable gas concentration level, said hyperbolic reference signal means effecting said hyperbolic signal in response to a threshold value of a preselected reference rate of change and an asymptotic value of a preselected reference rate of change; and comparator means for comparing the rate of change of said flammable gas concentration signal with the hyperbolic reference signal to determine when the rate of change of said flammable gas concentration level exceeds the preselected hyperbolic hazardous rate of change of said flammable gas concentration level.

5. A flammable gas detection system as in claim 4 further including switch means including a normally closed switch which opens when the flammable gas concentration signal exceeds said hyperbolic reference signal, and a second switch coupled to the normally closed switch; an integrator coupled to the second switch for effecting an integrated signal generally indicative of the time when the normally closed switch is open; second comparator means for comparing the integrated signal with a reference time signal; and control means operatively responsive to the second comparator means for energizing an alarm signal when the integrated signal exceeds the reference time signal whereby said alarm signal is energized only when said rate of change of said flammable gas concentration level occurs for a preselected period of time.

6. A method for monitoring the rate of change of flammable gas concentration level of a mixture of flammable gas and non-flammable gas, comprising the steps of:

detecting the rate of change of the flammable gas concentration level;
comparing the detected rate of change of the flammable gas concentration level with a preselected exponential reference rate of change of flammable gas concentration level; and
effecting a signal when the detected rate of change of the flammable gas concentration level exceeds the preselected exponential reference rate of change.

7. A method as in claim 6 further including the steps of sensing the magnitude of the flammable gas concentration level, comparing the magnitude with a reference magnitude of flammable gas concentration level, and inhibiting the signal when the sensed magnitude is less than the reference magnitude.

8. A method as in claim 7 further including the steps of producing a first voltage output when the period of time in which the detected rate of change of the flammable gas concentration level exceeds the preselected exponential reference rate of change, comparing the period of time to a predetermined period of time, and inhibiting the signal when the period of time of the detected rate of change is less than the predetermined period of time.

9. A method as in claim 7 further including selecting a threshold value, selecting an asymptotic value, and generating said preselected exponential reference rate of change proportional to said threshold value and said asymptotic value.

* * * * *

UNITED STATES PATENT AND TRADEMARK OFFICE
CERTIFICATE OF CORRECTION

PATENT NO. : 4,074,243
DATED : February 14, 1978
INVENTOR(S) : John S. Bogen and Gary I. Robin It is certified that error appears in the above-identified patent and that said Letters Patent are hereby corrected as shown below:

Col. 2, l. 63          "illutrating" should be --illustrating--
Col. 5, l. 15          "preselected" should be --predetermined--
Col. 5, l. 26          "asumptote" should be --asymptote--
Col. 5, l. 30          after "0.1" insert --to about 1--
Col. 6, l. 49          after "flammable" insert --gas--

Signed and Sealed this

Thirtieth Day of May 1978

[SEAL]

Attest:

RUTH C. MASON          LUTRELLE F. PARKER
*Attesting Officer*      *Acting Commissioner of Patents and Trademarks*